US008889735B2

(12) United States Patent
Ueno

(10) Patent No.: US 8,889,735 B2
(45) Date of Patent: Nov. 18, 2014

(54) METHOD FOR TREATING ASTHENOPIA

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 0 days.

(21) Appl. No.: 13/441,474

(22) Filed: Apr. 6, 2012

(65) Prior Publication Data

US 2012/0259008 A1   Oct. 11, 2012

Related U.S. Application Data

(60) Provisional application No. 61/472,875, filed on Apr. 7, 2011.

(51) Int. Cl.
A61K 31/215 (2006.01)
A61K 31/5575 (2006.01)
A61K 9/00 (2006.01)

(52) U.S. Cl.
CPC ........... *A61K 31/5575* (2013.01); *A61K 9/0048* (2013.01); *Y10S 514/912* (2013.01)
USPC .......................................... 514/530; 514/912

(58) Field of Classification Search
None
See application file for complete search history.

(56) References Cited

U.S. PATENT DOCUMENTS

| | | | |
|---|---|---|---|
| 5,001,153 A | 3/1991 | Ueno et al. | |
| 5,073,569 A | 12/1991 | Ueno et al. | |
| 5,106,869 A | 4/1992 | Ueno et al. | |
| 5,151,444 A | 9/1992 | Ueno et al. | |
| 5,166,174 A | 11/1992 | Ueno et al. | |
| 5,166,178 A | 11/1992 | Ueno et al. | |
| 5,194,429 A | 3/1993 | Ueno et al. | |
| 5,212,324 A | 5/1993 | Ueno | |
| 5,221,690 A | 6/1993 | Sugiyama et al. | |
| 5,221,763 A | 6/1993 | Ueno et al. | |
| 5,225,439 A | 7/1993 | Ueno et al. | |
| 5,236,907 A | 8/1993 | Ueno et al. | |
| 5,380,709 A | 1/1995 | Ueno et al. | |
| 5,428,062 A | 6/1995 | Ueno et al. | |
| 5,534,547 A | 7/1996 | Ueno et al. | |
| 5,591,887 A | 1/1997 | Ueno et al. | |
| 5,686,487 A | 11/1997 | Ueno | |
| 5,739,161 A | 4/1998 | Ueno | |
| 5,770,759 A | 6/1998 | Ueno et al. | |
| 5,773,471 A | 6/1998 | Oguchi et al. | |
| 5,886,034 A | 3/1999 | Ueno et al. | |
| 6,242,485 B1 | 6/2001 | Ueno | |
| 6,265,440 B1 | 7/2001 | Ueno et al. | |
| 2003/0060511 A1 | 3/2003 | Ueno | |
| 2011/0020448 A1 | 1/2011 | Park et al. | |

FOREIGN PATENT DOCUMENTS

| | | |
|---|---|---|
| JP | 9-87179 A | 3/1997 |
| JP | 2004-521960 A | 7/2004 |
| JP | 2011-507831 A | 3/2011 |
| WO | 2008/023784 A1 | 2/2008 |

OTHER PUBLICATIONS

International Search Report and Written Opinion for PCT/JP2012/060094 dated May 29, 2012.
Katsumura, K. et al.; Effects of latanoprost instillation on the accommodation and pupil size in normal young adults; Rinsho Ganka, 2001, vol. 55, No. 2, pp. 221-225.
Tezuka, H. et al.; A mechanism for reducing intraocular pressure in normal volunteers using UF-021, a prostaglandin-related compound; Nihon Ganka Gakkai Zasshi, 1992, vol. 96, No. 4, pp. 496-500.
International Preliminary Report on Patentability for Application No. PCT/JP2012/060094 dated Oct. 8, 2013.

*Primary Examiner* — Savitha Rao
*Assistant Examiner* — Gregg Polansky
(74) *Attorney, Agent, or Firm* — Sughrue Mion, PLLC

(57) ABSTRACT

The present invention relates to a method for treating asthenopia, accommodative dysfunction or ocular pain comprising an administration of a specific prostaglandin compound to a mammalian subject. The present invention also relates to a composition for treating asthenopia, accommodative dysfunction or ocular pain comprising a specific prostaglandin compound.

9 Claims, No Drawings

METHOD FOR TREATING ASTHENOPIA

TECHNICAL FIELD

The present invention relates to a method for prophylactic and therapeutic treatment of asthenopia.

BACKGROUND

Asthenopia is characterized by weakness or fatigue of the eyes, often accompanied by eye pain, red eyes, headache, dimming or blurring of vision and intermittent double vision. These symptoms tend to occur after tedious visual tasks such as reading or computer work. Asthenopia may be due to refractive errors, accommodation errors or abnormalities in monocular or binocular vision including myopia (nearsightedness or shortsightedness), presbyopia, farsightedness and astigmatism. Conventional treatments include the use of the eye drops containing Vitamin B1, B6 or B12, but it is not satisfied treatment.

Fatty acid derivatives are members of class of organic carboxylic acids, which are contained in tissues or organs of human or other mammals, and exhibit a wide range of physiological activity. Some fatty acid derivatives found in nature generally have a prostanoic acid skeleton as shown in the formula (A):

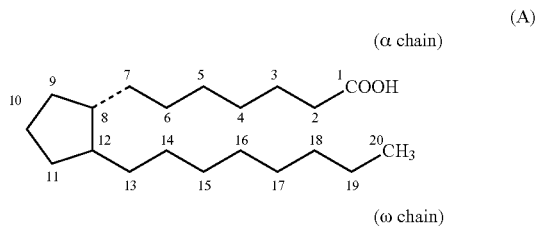 [SMILES: CCCCCCCCC1CCC[C@@H]1CCCCCCC(=O)O]

On the other hand, some of synthetic prostaglandin (PG) analogues have modified skeletons. The primary PGs are classified into PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:
Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

PGs are known to have various pharmacological and physiological activities, for example, vasodilatation, inducing of inflammation, platelet aggregation, stimulating uterine muscle, stimulating intestinal muscle, anti-ulcer effect and the like.

PGs have been known as drugs used in the ophthalmic field, for example, for lowering intraocular pressure or treating glaucoma. For example, (+)-Isopropyl (Z)-7-[(1R,2R,3R, 5S)-3,5-dihydroxy-2-[(3R)-3-hydroxy-5-phenylpentyl]cyclopentyl]-5-heptenoate (general name: latanoprost), Isopropyl (5Z)-7-((1R,2R,3R,5S)-3,5-dihydroxy-2-({1E, 3R)-3-hydroxy-4-[3-(trifluoromethyl) phenoxy]but-1-enyl}cyclopentyl)hept-5-enoate (general name: travoprost), (5Z)-7-{(1R,2R,3R,5S)-3,5-Dihydroxy-2-[(1E,3S)-3-hydroxy-5-phenylpent-1-en-1-yl]cyclopentyl}-N-ethylhept-5-enamide (general name: bimatoprost) and 1-Methylethyl (5Z)-7-{(1R,2R,3R,5S)-2-[(1E)-3,3-difluoro-4-phenoxy-1-butenyl]-3,5-dihydroxy cyclopentyl}-5-heptenoate (general name: tafluprost) have been marketed as ophthalmic solution for the treatment of glaucoma and/or ocular hypertension under the name of Xalatan®, Travatan®, Lumigan® and Tapros®, respectively.

Prostones, having an oxo group at position 15 of prostanoic acid skeleton (15-keto type) and having a single bond between positions 13 and 14 and an oxo group at position 15 (13,14-dihydro-15-keto type), are fatty acid derivatives known as substances naturally produced by enzymatic actions during metabolism of the primary PGs and have some therapeutic effect. Prostones have been disclosed in U.S. Pat. Nos. 5,073,569, 5,534,547, 5,225,439, 5,166,174, 5,428,062 5,380,709 5,886,034 6,265,440, 5,106,869, 5,221,763, 5,591, 887, 5,770,759 and 5,739,161, the contents of these references are herein incorporated by reference.

Prostones have also been known to be useful in the ophthalmic field, for example, for lowering intraocular. pressure and treating glaucoma (U.S. Pat. Nos. 5,001,153, 5,151,444, 5,166,178, 5,194,429 and 5,236,907), for treating cataract (U.S. Pat. Nos. 5,212,324 and 5,686,487), for increasing the choroidal blood flow (U.S. Pat. No. 5,221,690), for treating optic nerve disorder (U.S. Pat. No. 5,773,471), the contents of these references are herein incorporated by reference. Ophthalmic solution comprising (+)-isopropyl (Z)-7-[(1R,2R,3R, 5S)-3,5-dihydroxy-2-(3-oxodecyl)cyclopentyl]hept-5-enoate (general name: isopropyl unoprostone) has been marketed under the name of Rescula® as a pharmaceutical product for the treatment of glaucoma and ocular hypertension.

However it is not known how fatty acid derivatives act on asthenopia.

DISCLOSURE OF THE INVENTION

In one aspect, the present invention provides a method for the treatment of asthenopia in a mammalian subject, which comprises administering to the subject in need thereof an effective amount of a fatty acid derivative represented by the formula (I):

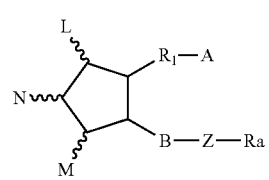

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH$_3$, or —CH$_2$OH, —COCH$_2$OH, —COOH or a functional derivative thereof;

B is single bond, —CH$_2$—CH$_2$—, —CH=CH—, —C≡C—, —CH$_2$—CH$_2$—CH$_2$—, —CH=CH—CH$_2$—, —CH$_2$—CH=CH—, —C≡C—CH$_2$— or —CH$_2$—C≡C—;

Z is

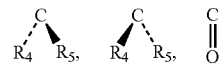

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$R_1$ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower) alkyloxy; aryl; aryloxy; heterocyclic group; heterocyclic-oxy group, and at least one of carbon atom in the aliphatic hydrocarbon is optionally substituted by oxygen, nitrogen or sulfur.

In another aspect, the present invention provides a method for the treatment of accommodative dysfunction in a mammalian subject, which comprises administering to the subject in need thereof an effective amount of a fatty acid derivative represented by the formula (I) wherein L, M, N, A, B, Z, $R_1$ and Ra are as described above.

In another aspect, the present invention provides a method for the treatment of ocular pain in a mammalian subject, which comprises administering to the subject in need thereof an effective amount of a fatty acid derivative represented by the formula (I) wherein L, M, N, A, B, Z, $R_1$ and Ra are as described above.

In further aspect, the present invention provides a pharmaceutical composition for the treatment described above, which comprises an effective amount of a fatty acid derivative represented by the formula (I) wherein L, M, N, A, B, Z, $R_1$ and Ra are as described above.

In still further aspect, the present invention provides use of an effective amount of a fatty acid derivative represented by the formula (I) wherein L, M, N, A, B, Z, $R_1$ and Ra are as described above for the preparation of a pharmaceutical composition for the treatment described above or in the treatment described above.

DETAILED DESCRIPTION OF THE INVENTION

The nomenclature of the fatty acid derivative used herein is based on the numbering system of the prostanoic acid represented in the above formula (A).

The formula (A) shows a basic skeleton of the C-20 fatty acid derivative, but the present invention is not limited to those having the same number of carbon atoms. In the formula (A), the numbering of the carbon atoms which constitute the basic skeleton of the fatty acid derivatives starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of carboxy group (C-1). Similarly, when the number of carbon atoms is decreased in the ω-chain, the number is deleted in the order starting from position 20; and when the number of carbon atoms is increased in the ω-chain, the carbon atoms at the position 21 or later are named as a substituent at position 20. Stereochemistry of the compounds is the same as that of the above formula (A) unless otherwise specified.

In general, each of PGD, PGE and PGF represents a fatty acid derivative having hydroxy groups at positions 9 and/or 11, but in the present specification they also include those having substituents other than the hydroxy groups at positions 9 and/or 11. Such compounds are referred to as 9-deoxy-9-substituted-fatty acid derivatives or 11-deoxy-11-substituted-fatty acid derivatives. A fatty acid derivative having hydrogen in place of the hydroxy group is simply named as 9- or 11-deoxy-fatty acid derivative.

As stated above, the nomenclature of a fatty acid derivative is based on the prostanoic acid skeleton. In the case the compound has similar partial structure as the primary PG, the abbreviation of "PG" may be used. Thus, a fatty acid derivative whose α-chain is extended by two carbon atoms, that is, having 9 carbon atoms in the α-chain is named as 2-decarboxy-2-(2-carboxyethyl)-PG compound. Similarly, a fatty acid derivative having 11 carbon atoms in the α-chain is named as 2-decarboxy-2-(4-carboxybutyl)-PG compound. Further, a fatty acid derivative whose ω-chain is extended by two carbon atoms, that is, having 10 carbon atoms in the ω-chain is named as 20-ethyl-PG compound. These compounds, however, may also be named according to the IUPAC nomenclatures.

Examples of the analogues including substitution compounds or derivatives of the above described fatty. acid derivative include a fatty acid derivative whose carboxy group at the end of the alpha chain is esterified; a fatty acid derivative whose a chain is extended, a physiologically acceptable salt thereof, a fatty acid derivative having a double bond between positions 2 and 3 or a triple bond between positions 5 and 6; a fatty acid derivative having substituent(s) on carbon atom(s) at position(s) 3, 5, 6, 16, 17, 18, 19 and/or 20; and a fatty acid derivative having a lower alkyl or a hydroxy (lower) alkyl group at position 9 and/or 11 in place of the hydroxy group.

According to the present invention, preferred substituents on the carbon atom at position(s) 3, 17, 18 and/or 19 include alkyl having 1-4 carbon atoms, especially methyl and ethyl. Preferred substituents on the carbon atom at position 16 include lower alkyls such as methyl and ethyl, hydroxy, halogen atom such as chlorine and fluorine, and aryloxy such as trifluoromethylphenoxy. Preferred substituents on the carbon atom at position 17 include lower alkyl such as methyl and ethyl, hydroxy, halogen atom such as chlorine and fluorine, and aryloxy such as trifluoromethylphenoxy. Preferred substituents on the carbon atom at position 20 include saturated or unsaturated lower alkyl such as $C_{1-4}$ alkyl, lower alkoxy such as $C_{1-4}$ alkoxy, and lower alkoxy alkyl such as $C_{1-4}$ alkoxy-$C_{1-4}$ alkyl. Preferred substituents on the carbon atom at position 5 include halogen atoms such as chlorine and fluorine. Preferred substituents on the carbon atom at position 6 include an oxo group forming a carbonyl group. Stereochemistry of PGs having hydroxy, lower alkyl or hydroxy (lower)alkyl substituent on the carbon atom at positions 9 and 11 may be α, β or a mixture thereof.

Further, the above described analogues or derivatives may have a ω chain shorter than that of the primary PGs and a substituent such as alkoxy, cycloalkyl, cycloalkyloxy, phenoxy and phenyl at the end of the truncated ω-chain.

A fatty acid derivative used in the present invention is represented by the formula (I):

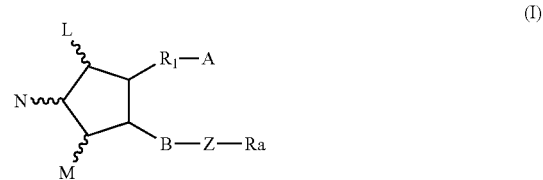

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH₃, or —CH₂OH, —COCH₂OH, —COOH or a functional derivative thereof;

B is single bond, —CH₂—CH₂—, —CH═CH—, —C≡C—, —CH₂—CH₂—CH₂—, —CH═CH—CH₂—, —CH₂—CH═CH—, —C≡C—CH₂— or —CH₂—C≡C—;

Z is

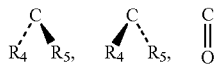

or single bond wherein R₄ and R₅ are hydrogen, hydroxy, halogen, lower alkyl, lower alkoxy or hydroxy(lower)alkyl, wherein R₄ and R₅ are not hydroxy and lower alkoxy at the same time;

R₁ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

A preferred compound used in the present invention is represented by the formula (II):

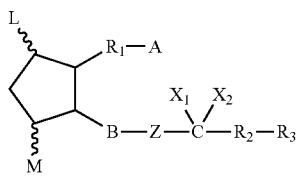

(II)

wherein L and M are hydrogen atom, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH₃, or —CH₂OH, —COCH₂OH, —COOH or a functional derivative thereof;

B is single bond, —CH₂—CH₂—, —CH═CH—, —C≡C—, —CH₂—CH₂—CH₂—, —CH═CH—CH₂—, —CH₂—CH═CH—, —C≡C—CH₂— or —CH₂—C≡C—;

Z is

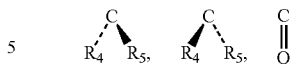

or single bond wherein R₄ and R₅ are hydrogen, hydroxy, halogen, lower alkyl, lower alkoxy or hydroxy(lower)alkyl, wherein R₄ and R₅ are not hydroxy and lower alkoxy at the same time;

X₁ and X₂ are hydrogen, lower alkyl, or halogen;

R₁ is a saturated or unsaturated bivalent lower or medium aliphatic hydrocarbon residue, which is unsubstituted or substituted with halogen, lower alkyl, hydroxy, oxo, aryl or heterocyclic group, and at least one of carbon atom in the aliphatic hydrocarbon is optionally substituted by oxygen, nitrogen or sulfur;

R₂ is a single bond or lower alkylene; and

R₃ is lower alkyl, lower alkoxy, lower alkanoyloxy, cyclo(lower)alkyl, cyclo(lower)alkyloxy, aryl; aryloxy, heterocyclic group or heterocyclic-oxy group, and at least one of carbon atom in the aliphatic hydrocarbon is optionally substituted by oxygen, nitrogen or sulfur.

In the above formula, the term "unsaturated" in the definitions for R₁ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout. the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl; propyl, isopropyl, butyl, isobutyl, L-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl.

The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower) alkyl ester such as hydroxyethyl ester; lower alkoxy (lower) alkyl esters such as methoxymethyl ester and 1-methoxyethyl ester; and optionally substituted aryl esters such as, for example, phenyl ester; tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or arylsulfonylamides such as methylsulfonylamide, ethylsulfonylamide and tolylsulfonylamide.

Preferred examples of L and M include hydrogen, hydroxy and oxo, and especially, L and M are both hydroxy, or L is oxo and M is hydrogen or hydroxy.

Preferred example of A is —COOH, its pharmaceutically acceptable salt, ester or amide thereof.

Preferred example of $X_1$ and $X_2$ are both being halogen atoms, and more preferably, fluorine atoms, so called 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur.

Examples of $R_1$ include, for example, the following groups:

—CH$_2$—CH$_2$—CH$_2$—CH$_2$—CH$_2$—CH$_2$—,
—CH$_2$—CH=CH—CH$_2$—CH$_2$—CH$_2$—,
—CH$_2$—CH$_2$—CH$_2$—CH$_2$—CH=CH—,
—CH$_2$—C≡C—CH$_2$—CH$_2$—CH$_2$—,
—CH$_2$—CH$_2$—CH$_2$—CH$_2$—O—CH$_2$—,
—CH$_2$—CH=CH—CH$_2$—O—CH$_2$—,
—CH$_2$—C≡C—CH$_2$—O—CH$_2$—,
—CH$_2$—CH$_2$—CH$_2$—CH$_2$—CH$_2$—CH$_2$—CH$_2$—,
—CH$_2$—CH=CH—CH$_2$—CH$_2$—CH$_2$—CH$_2$—,
—CH$_2$—CH$_2$—CH$_2$—CH$_2$—CH$_2$—CH=CH—,
—CH$_2$—C≡C—CH$_2$—CH$_2$—CH$_2$—CH$_2$—,
—CH$_2$—CH$_2$—CH$_2$—CH$_2$—CH$_2$—CH(CH$_3$)—CH$_2$—,
—CH$_2$—CH$_2$—CH$_2$—CH$_2$—CH(CH$_3$)—CH$_2$—,
—CH$_2$—CH$_2$—CH$_2$—CH$_2$—CH$_2$—CH$_2$—CH$_2$—CH$_2$—,
—CH$_2$—=CH—CH$_2$—CH$_2$—CH$_2$—CH$_2$—CH$_2$—,
—CH$_2$—CH$_2$—CH$_2$—CH$_2$—CH$_2$—CH$_2$—=CH—,
—CH$_2$—C≡C—CH$_2$—CH$_2$—CH$_2$—CH$_2$—CH$_2$—, and
—CH$_2$—CH$_2$—CH$_2$—CH$_2$—CH$_2$—CH$_2$—CH(CH$_3$)—CH$_2$—.

Preferred Ra is a hydrocarbon containing 1-10 carbon atoms, more preferably, 1-8 carbon atoms. Ra may have one or two side chains having one carbon atom. Further, at least one carbon atom in the aliphatic hydrocarbon is optionally substituted by oxygen, nitrogen or sulfur.

A typical example of fatty acid derivative in this invention is (Z)-7-[(1R,2R,3R,5S)-3,5-dihydroxy-2-(3-oxodecyl)cyclopentyl]hept-5-enoic acid and its derivatives or analogues. The most favorable example of fatty acid derivative in this invention is (+)-isopropyl (Z)-7-[(1R,2R,3R,5S)-3,5-dihydroxy-2-(3-oxodecyl)cyclopentyl]hept-5-enoate (hereinafter, isopropyl unoprostone).

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the fatty acid derivative which is dihydro between 13 and 14, and keto(=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the fatty acid derivatives used in the invention include the bicyclic compound and analogs or derivatives thereof.

The bicyclic compound is represented by the formula (III)

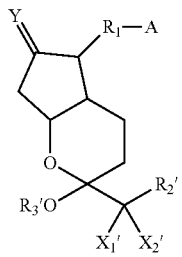

(III)

wherein, A is —$CH_3$, or —$CH_2OH$, —$COCH_2OH$, —COOH or a functional derivative thereof;

$X_1'$ and $X_2'$ are hydrogen, lower alkyl, or halogen;

Y is

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkyl, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group, and at least one of carbon atom in the aliphatic hydrocarbon is optionally substituted by oxygen, nitrogen or sulfur.

$R_3'$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073, 569, 5,166,174, 5,221,763, 5,212,324, 5,739,161 and 6,242, 485 (these cited references are herein incorporated by reference).

According to the present invention, a mammalian subject may be treated by the instant invention by administering the compound used in the present invention. The subject may be any mammalian subject including a human. The compound can be applied systemically or topically. Usually, the compound may be administered by oral administration, intravenous injection (including infusion), ocular topical administration (e.g. periocular (e.g., subTenon's), subconjunctival, intraocular, intravitreal, intracameral, subretinal, suprachoroidal, and retrobulbar administrations) and the like.

The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.00001-500 mg/kg per day, more preferably 0.0001-100 mg/kg per day.

The compound may preferably be formulated in a pharmaceutical composition suitable for administration in a conventional manner. The composition may be those suitable for oral administration, ocular topical administration, injection or perfusion as well as it may be an external agent.

The composition of the present invention may further contain physiologically acceptable additives. Said additives may include the ingredients used with the present compounds such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin. and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.000001-10.0%, more preferably 0.00001-5.0%, most preferably 0.0001-1%.

Examples solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary.

They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. Purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of injectable compositions of the present invention for parenteral administration include sterile aqueous or non-aqueous solutions, suspensions and emulsions.

Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization.

The injectable composition may also be provided as a sterilized powder composition to be dissolved in sterilized solvent for injection before use.

The present compound may also be formulated as ophthalmic composition such as eye drops and eye ointments. The form may include all ophthalmic formulations for ocular topical administration used in the ophthalmic field.

The eye drops are prepared by dissolving active ingredients in a sterile aqueous solution such as saline and buffering solution. The eye drops may be provided as a powder composition to be dissolved before use, or by combining powder compositions to be dissolved before use. The eye ointments are prepared by mixing the active ingredient into an ointment base. The formulations are prepared according to the conventional methods.

Osmolarity modifiers include sodium chloride, potassium chloride, calcium chloride, sodium bicarbonate, sodium carbonate, magnesium sulfate, sodium hydrogen phosphate, sodium dihydrogen phosphate, dipotassium hydrogen phosphate, boric acid, borax, sodium hydroxide, hydrochloric acid, mannitol, isosorbitol, propylene glycol, glucose and glycerine, but not limited thereto, as far as they are ordinarily used in the ophthalmic field.

Further, additives ordinarily used in the ophthalmic field may be added to the present composition as desired. Such additives include, for example, buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, etc.), all of which are included herein by reference.

In preparing the present composition as an eye ointment, other than the above additives, the composition may contain ordinarily used eye ointment base. Such eye ointment base includes, but not limited to, oil base such as vaseline, liquid paraffin, polyethylene, selen 50, plastibase, macrogol or a combination thereof; emulsion base having oil phase and water phase emulsified with surfactant, etc.; and water soluble base such as hydroxypropylmethylcellulose, carboxypropylmethylcellulose, polyethylene glycol, etc.

According to the present invention, the preferable embodiment includes that ophthalmic composition contains substantially no benzalkonium chloride. The phrase of the ophthalmic composition contains substantially no benzalkonium chloride used herein means that the composition contains no benzalkonium chloride, or the composition contains benzalkonium chloride as low as possible. In the present invention, the ophthalmic composition may contain benzalkonium chloride at a concentration of less than 0.01%, preferably 0.005% or less, more preferably 0.003% or less.

The present eye drops may be formulated as a sterile unit dose type formulation (one day type or single unit dose type) containing no preservatives such as benzalkonium chloride.

The ophthalmic composition further includes sustained release forms such as gel formulation, liposome formulation, lipid microemulsion formulation, microsphere formulation, nanosphere formulation and implant formulation in order to provide the active compound sustainedly to the back of the eye.

The concentration and administration number of the active ingredient of the eye drops used in the present invention vary according to the compound to be used, the kind of subjects (such as animals or humans), age, weight, symptoms to be treated, effects of treatment to be desired, administration methods, administration volume, period of treatment, etc. Accordingly, suitable concentration and administration number may be chosen as desired. Taking an example of isopropyl unoprostone, which is one form of the present invention, the formulation containing 0.0001-1.0%, preferably 0.001-0.5%, for example, 0.001-0.15% or 0.001-0.06% of isopropyl unoprostone may be ordinarily administered to an adult 1-10 times a day.

Some of the ophthalmic composition used in the present invention may be prepared by the method disclosed in US publication No. 2011/0275715 (these cited references is herein incorporated by reference).

According to the present invention, the fatty acid derivatives of the present invention are useful for treating asthenopia.

As used herein, asthenopia refers to an ophthalmological condition where symptoms such as fatigue of the eyes, pain of the eyes, blurred vision, red eye (hyperemia), intermittent double vision, headache, shoulder stiffness and nausea appear. The symptoms may appear after. reading, computer work, or other close activities that involve tedious visual tasks.

Since asthenopia is characterized by weakness or fatigue of the eyes, often accompanied by eye pain, red eyes, headache, dimming or blurring of vision and intermittent double vision, the present invention further includes the treatment of one or more symptoms or conditions associated with or accompanied by asthenopia. Examples of the symptoms or conditions associated with or accompanied by asthenopia include, but are not limited to, eye pain, red eyes, headache, dimming or blurring of vision, intermittent double vision, eye discharge, accommodative dysfunction, impairment in adaptation to brightness and darkness, ocular motility disorder or impaired motor function of muscle around eye such as blepharospasm and any combination of them.

In addition, according to the present invention, the fatty acid derivatives of the present invention are useful for improving accommodation ability and treating accommodative dysfunction.

As used herein, "accommodation" refers to the process by which the vertebrate eye changes optical power to maintain a clear image (focus) on an object as its distance varies. Examples of accommodation dysfunction include, but are not limited to myopia (nearsightedness or shortsightedness), presbyopia, hyperopia (i.e. farsightedness), astigmatism, cycloplegia and accommodative spasm.

In one embodiment, the fatty acid derivatives of the present invention are useful for improving ability of ciliary muscle to focus on an object as the distance varies.

In another embodiment, the fatty acid derivatives of the present invention are useful for treating accommodative asthenopia. "Accommodative asthenopia" which is one type of asthenopia, can be caused by refractive error (e.g. myopia (nearsightedness or shortsightedness), hyperopia (i.e. farsightedness), astigmatism, use of contact lenses or eye glasses which are not adjusted for one's eyesight) or accommodation error (e.g. presbyopia, cycloplegia, accommodative spasm).

It is known that the patients with Parkinson's disease have asthenopia and accommodative dysfunctions including or derived from blepharospasm, paucity of blinking, apraxia of lid opening, reduced vergence, reduced upgaze, blurred vision, upgaze deficiency, convergence insufficiency.

In further aspect of the present invention, the fatty acid derivatives of the present invention are useful for treating asthenopia and accommodative dysfunctions in a subject suffering from Parkinson's disease. The asthenopia and accommodative dysfunctions seen in a subject suffering from Parkinson's disease, which can be treated by the fatty acid derivatives of the present invention, may be caused by etiology of Parkinson's disease oranti-Parkinson's diseases drug administered to a subject (e.g. dopamine receptor agonist Cabergoline), anticholinergic drug (e.g. trihexyphenidyl hydrochloride)); or both of them. Examples of the symptoms or conditions associated with or accompanied by asthenopia and Examples of accommodative dysfunctions seen in a subject suffering from Parkinson's, disease are the same with those as described above.

In further aspect of the present invention, the fatty acid derivatives of the present invention are useful for treating eye pain.

Based on the method which is provided by the present invention, the skilled person can understand that a pharmaceutical composition which is useful for the method is prepared; that the compound described above is used for the preparation of a pharmaceutical composition which is useful for the method; and that the compound described above is used in the treatment of the disease described above. Thus, according to the present invention, a pharmaceutical composition comprising the compound described above for the treatment of the disease described above; use of the compound described above for preparation of a pharmaceutical composition for the treatment of the disease described above; and, use of the compound described above in the treatment of the disease described above etc are also provided.

The term "treating" or "treatment" used herein includes prophylactic and therapeutic treatment, and any means of control such as prevention, care, relief of the condition, attenuation of the condition, arrest of progression, etc.

The pharmaceutical composition of the present invention may contain a single active ingredient or a combination of two or more active ingredients, as far as they are not contrary to the objects of the present invention. In a combination of plural active ingredients, their respective contents may be suitably increased or decreased in consideration of their therapeutic effects and safety.

The present invention will be described in detail with reference to the following example, which, however, is not intended to limit the scope of the present invention.

Example 1

A subject who had blurring of vision received eye drop comprising 0.12% isopropyl unoprostone. After single administration of it, eye discharge and blurry vision were improved. On the other hand, after single administration of placebo, eye discharge and blurry vision were not improved.

Example 2

A subject who had eye pain received eye drop comprising 0.12% isopropyl unoprostonen. After single administration of it, eye pain was improved. On the other hand, after single administration of placebo, eye pain was not improved.

Example 3

A subject who was difficult to focus on the objects even using the farsighted glasses received eye drop comprising 0.12% isopropyl unoprostone twice a day. He was presbyopia and astigmatism. After seven days administration of it, he was able to focus on the objects easier and quicker than before the administration, and the improvement was continued for three weeks.

The result indicates that the present compound is useful for improving the accommodative function.

What is claimed is:

1. A method for treating asthenopia in a mammalian subject, which comprises administering to the subject in need thereof an effective amount of isopropyl unoprostone.

2. The method as described in claim 1, wherein eye pain, eye discharge or blurry vision associated with or accompanied by said asthenopia is treated.

3. The method as described in claim 1, wherein the asthenopia is accommodative asthenopia.

4. The method as described in claim 1, wherein presbyopia, farsightedness or astigmatism associated with or accompanied by said asthenopia is treated.

5. The method as described in claim 1, wherein said isopropyl unoprostone is formulated as a composition for topical administration.

6. The method as described in claim 5, wherein said composition is an ophthalmic composition for ocular topical administration.

7. The method as described in claim 6, wherein said ophthalmic composition is formulated as eye drop.

8. The method as described in claim 7, wherein said eye drop is formulated as a sterile unit dose type containing no preservatives.

9. The method as described in claim 8, wherein said ophthalmic composition comprises substantially no benzalkonium chloride.

* * * * *